(12) United States Patent
Takeuchi et al.

(10) Patent No.: US 12,306,161 B2
(45) Date of Patent: May 20, 2025

(54) DETECTION DEVICE AND ELECTRONIC APPARATUS

(71) Applicant: Sharp Semiconductor Innovation Corporation, Nara (JP)

(72) Inventors: Noboru Takeuchi, Nara (JP); Daiki Naruse, Nara (JP); Mitsutoshi Okami, Nara (JP); Hirokazu Sasabe, Nara (JP); Toshiya Fujiyama, Nara (JP); Yoshifumi Masuda, Nara (JP)

(73) Assignee: Sharp Semiconductor Innovation Corporation, Nara (JP)

( * ) Notice: Subject to any disclaimer, the term of this patent is extended or adjusted under 35 U.S.C. 154(b) by 225 days.

(21) Appl. No.: 18/084,151

(22) Filed: Dec. 19, 2022

(65) Prior Publication Data
US 2023/0194490 A1 Jun. 22, 2023

(30) Foreign Application Priority Data
Dec. 22, 2021 (JP) ................... 2021-208413

(51) Int. Cl.
*G01N 1/00* (2006.01)
*G01N 15/00* (2006.01)
*G01N 33/00* (2006.01)
(52) U.S. Cl.
CPC ......... *G01N 33/0032* (2013.01); *G01N 15/00* (2013.01); *G01N 2015/0046* (2013.01)

(58) Field of Classification Search
CPC ................. G01N 2015/0662; G01N 2015/084
See application file for complete search history.

(56) References Cited

U.S. PATENT DOCUMENTS

| | | | | |
|---|---|---|---|---|
| 6,030,428 A | * | 2/2000 | Ishino | B01D 39/1692 55/528 |
| 2015/0285517 A1 | * | 10/2015 | Scofield | F24F 11/30 702/50 |
| 2017/0226949 A1 | * | 8/2017 | Uchiyama | G01N 15/0656 |
| 2019/0331582 A1 | | 10/2019 | Mou et al. | |
| 2021/0087912 A1 | * | 3/2021 | Nagata | G01N 15/0272 |

FOREIGN PATENT DOCUMENTS

| | | | |
|---|---|---|---|
| DE | 3304324 A1 | * | 3/1991 |
| JP | 2017181153 A | | 10/2017 |
| JP | 2019215315 A | | 12/2019 |

* cited by examiner

*Primary Examiner* — Jamel E Williams
*Assistant Examiner* — Alex T Devito
(74) *Attorney, Agent, or Firm* — ScienBiziP, P.C.

(57) ABSTRACT

A detection device according to an aspect of the invention, includes: a housing including an air intake port and an air discharge port; a platelike member having a first air ventilation port and a second air ventilation port, the platelike member being provided inside the housing; a first sensor provided on an air intake port side of the first air ventilation port on a front face of the platelike member; and a second sensor provided between the first air ventilation port and the second air ventilation port on a rear face of the platelike member.

9 Claims, 14 Drawing Sheets

110: DETECTION DEVICE
140: PLATELIKE MEMBER
141: FIRST AIR VENTILATION PORT
142: SECOND AIR VENTILATION PORT
150: GAS CURRENT GENERATION MECHANISM
FP2: SECOND FLOW PATH
S1: FIRST SENSOR
S2: SECOND SENSOR
S3: THIRD SENSOR

110: DETECTION DEVICE
130: INNER COVER
133: PARTITION PLATE
140: PLATELIKE MEMBER
141: FIRST AIR VENTILATION PORT
190: THIRD AIR VENTILATION PORT
FP1: FIRST FLOW PATH
FP2: SECOND FLOW PATH
S1: FIRST SENSOR
S2: SECOND SENSOR

310: DETECTION DEVICE
340a: FIRST PLATELIKE MEMBER
340b: SECOND PLATELIKE MEMBER
390: THIRD AIR VENTILATION PORT
S2: SECOND SENSOR

DETECTION DEVICE AND ELECTRONIC APPARATUS

CROSS-REFERENCE TO RELATED APPLICATIONS

This application claims the benefit of priority to Japanese Patent Application Number 2021-208413 filed on Dec. 22, 2021. The entire contents of the above-identified application are hereby incorporated by reference.

BACKGROUND

1. Field

The present invention relates to detection devices and electronic apparatuses.

2. Description of the Related Art

Particle detection sensors have been developed for detecting PM 2.5 and other fine particles. Japanese Unexamined Patent Application Publication, Tokukai, No. 2019-215315 discloses a gas inspection device including a gas inspection module and a fine particle inspection module. Japanese Unexamined Patent Application Publication, Tokukai, No. 2017-181153 discloses a particle detection sensor that restrains air turbulence in the detection region.

To build, as a detection device, a multi-sensor unit incorporating, for example, a gas sensor (e.g., VOC sensor) and a temperature/humidity sensor as well as a particle detection sensor, the gas sensor and the temperature/humidity sensor need to be mounted along a flow path for the air that is subjected to detection by the particle detection sensor to collect information on the concentration of gas in the air outside the detection device and the temperature and humidity of the air.

SUMMARY

However, the air current inside the detection device contains dust and aerosols such as PM 2.5, and the dust could pile up on the surface of the sensors, disadvantageously causing the sensors to malfunction. Meanwhile, if the sensor (especially, the temperature/humidity sensor) is disposed along an air flow path, the sensor is so close to the light-emitting element of the particle detection sensor that the sensor can disadvantageously malfunction under the adverse effect of the heat generated by the light-emitting element.

The present invention, in an aspect thereof, has an object to prevent malfunction of a plurality of sensors in a detection device and reduce the size of such a detection device.

To address these issues, the present invention, in one aspect thereof, is directed to a detection device including: a housing including an air intake port and an air discharge port; a platelike member having a first air ventilation port and a second air ventilation port, the platelike member being provided inside the housing; a first sensor provided on an air intake port side of the first air ventilation port on a front face of the platelike member; and a second sensor provided between the first air ventilation port and the second air ventilation port on a rear face of the platelike member.

The present invention, in an aspect thereof, prevents malfunction of a plurality of sensors in a detection device and reduce the size of such a detection device.

DESCRIPTION OF THE EMBODIMENTS

Embodiment 1

The following will describe Embodiment 1 of the present invention in detail. Note that the direction of a longer side of the detection device is the X-direction, the direction of a shorter side of the detection device is the Y-direction, and the vertical direction of the detection device is the Z-direction, unless mentioned otherwise.

Figure 1:
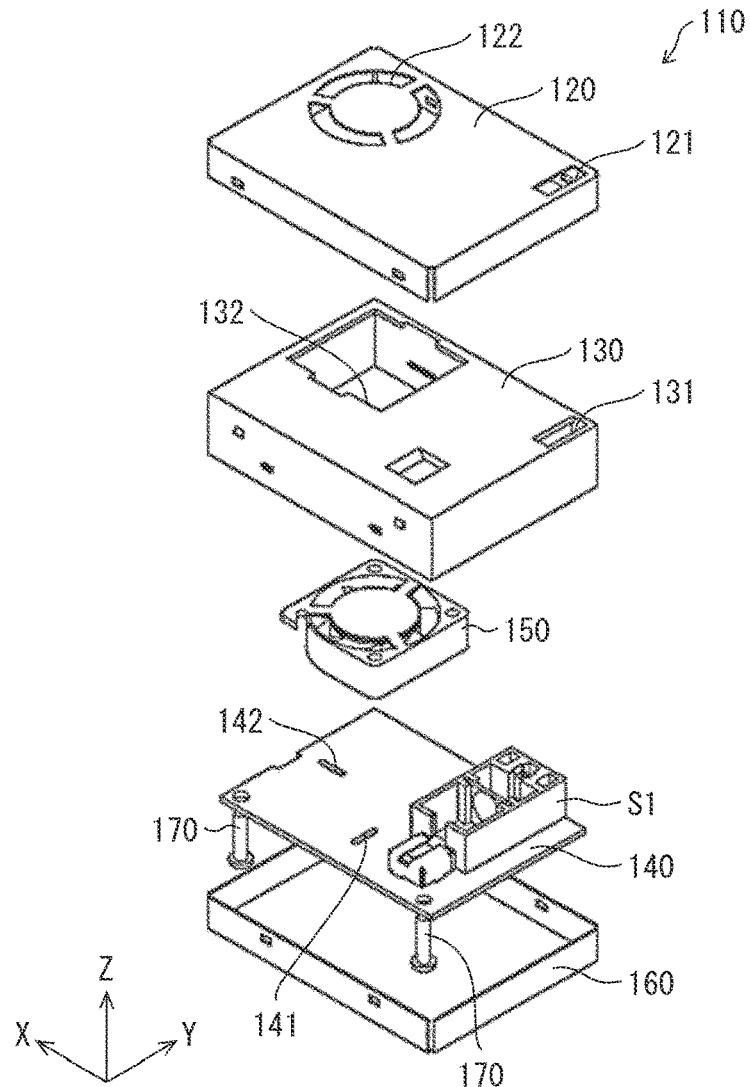
FIG. 1 is an exploded perspective view of a detection device in accordance with Embodiment 1 of the present invention.

FIG. 1 is an exploded perspective view of a detection device 110 in accordance with the present embodiment.

The detection device 110 is a multi-sensor device for detecting properties of gas. Examples of electronic apparatuses that can include the detection device 110 include air purifiers and air conditioners.

Figure 3:
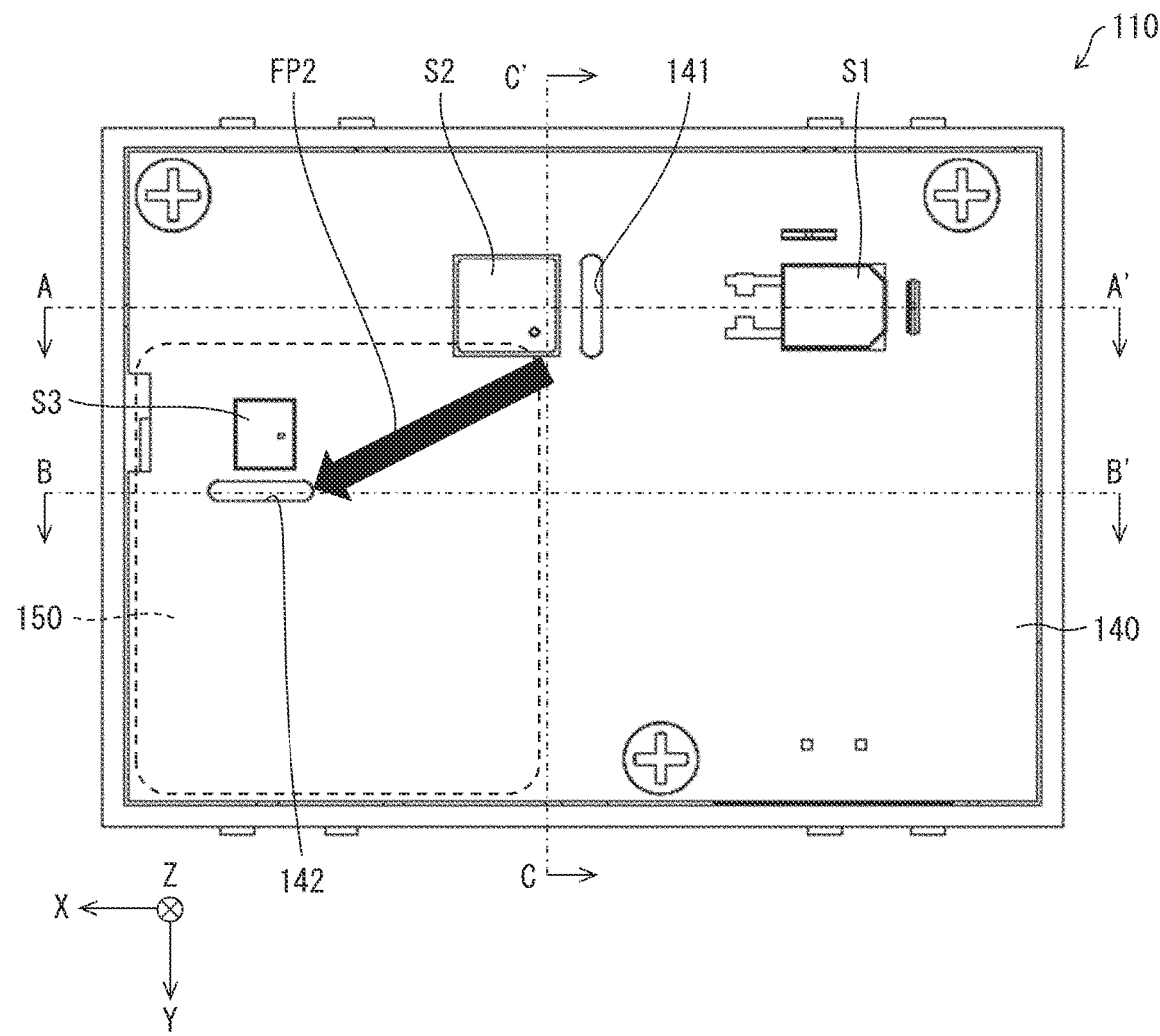
FIG. 3 is an illustration of a platelike member in accordance with Embodiment 1 of the present invention.

Referring to FIG. 1, the detection device 110 includes: a housing composed primarily of a front cover 120, an inner cover 130, and a rear cover 160; a platelike member 140; a gas current generation mechanism 150; a first sensor S1; a second sensor S2 (see FIG. 3); and a third sensor S3 (see FIG. 3).

The front cover 120 is a cover disposed on the front side and has an inlet (air intake port) 121 and an outlet (air discharge port) 122. The inlet 121 and the outlet 122 are provided in the rear face opposite the platelike member 140. The inlet 121 is a port through which gas is drawn into the detection device 110. The outlet 122 is a port through which gas is vented out of the detection device 110 and has a shape corresponding to the discharge port of the gas current generation mechanism 150.

The inner cover 130 is a cover disposed between the front cover 120 and the rear cover 160, covering the platelike member 140, the first sensor S 1, and the gas current generation mechanism 150. The inner cover 130 has an inlet (air intake port) 131 and an outlet (air discharge port) 132. The inlet 131 and the outlet 132 are provided in the rear face opposite the platelike member 140, in locations corresponding to the inlet 121 and the outlet 122 of the front cover 120. The inlet 131 is a port through which gas is drawn into the detection device 110. The outlet 132 is a port through which gas is vented out of the detection device 110 and has a shape corresponding to the profile of the gas current generation mechanism 150.

The platelike member 140 is a base plate to which the first sensor S1 and other components are mounted. The platelike member 140 may be a substrate. A "substrate" refers to a printed board including an insulating plate on or in which conducting wires are provided. The first sensor S1 is provided on the front face of the platelike member 140, on the inlet 131 side of a first air ventilation port 141.

Although shown as a separate component for convenience in FIG. 1, the gas current generation mechanism 150 is integrated to the inner cover 130 and generates an air current moving inside the housing from the inlet 131 toward the outlet 132. Thus, the gas current generation mechanism 150 vents air out of the housing through the outlet 132. The gas current generation mechanism 150 includes, for example, a fan, a temperature adjuster, and a pressure adjuster. Note that the gas current generation mechanism 150 is not necessarily provided inside the housing and may be provided outside the housing.

The rear cover 160 is a cover disposed in a lower portion of the detection device 110. Referring to FIG. 1, the gas current generation mechanism 150, which is integrated to the inner cover 130, and the rear cover 160 are provided so as to cover the platelike member 140 and the first sensor S1. To describe it in more detail, the platelike member 140 is supported via screws 170 provided inside the rear cover 160. The inner cover 130, which is integrated to the gas current generation mechanism 150, covers the platelike member 140.

The platelike member 140 has formed therein the first air ventilation port 141 and a second air ventilation port 142. Details will be given later.

Figure 2:
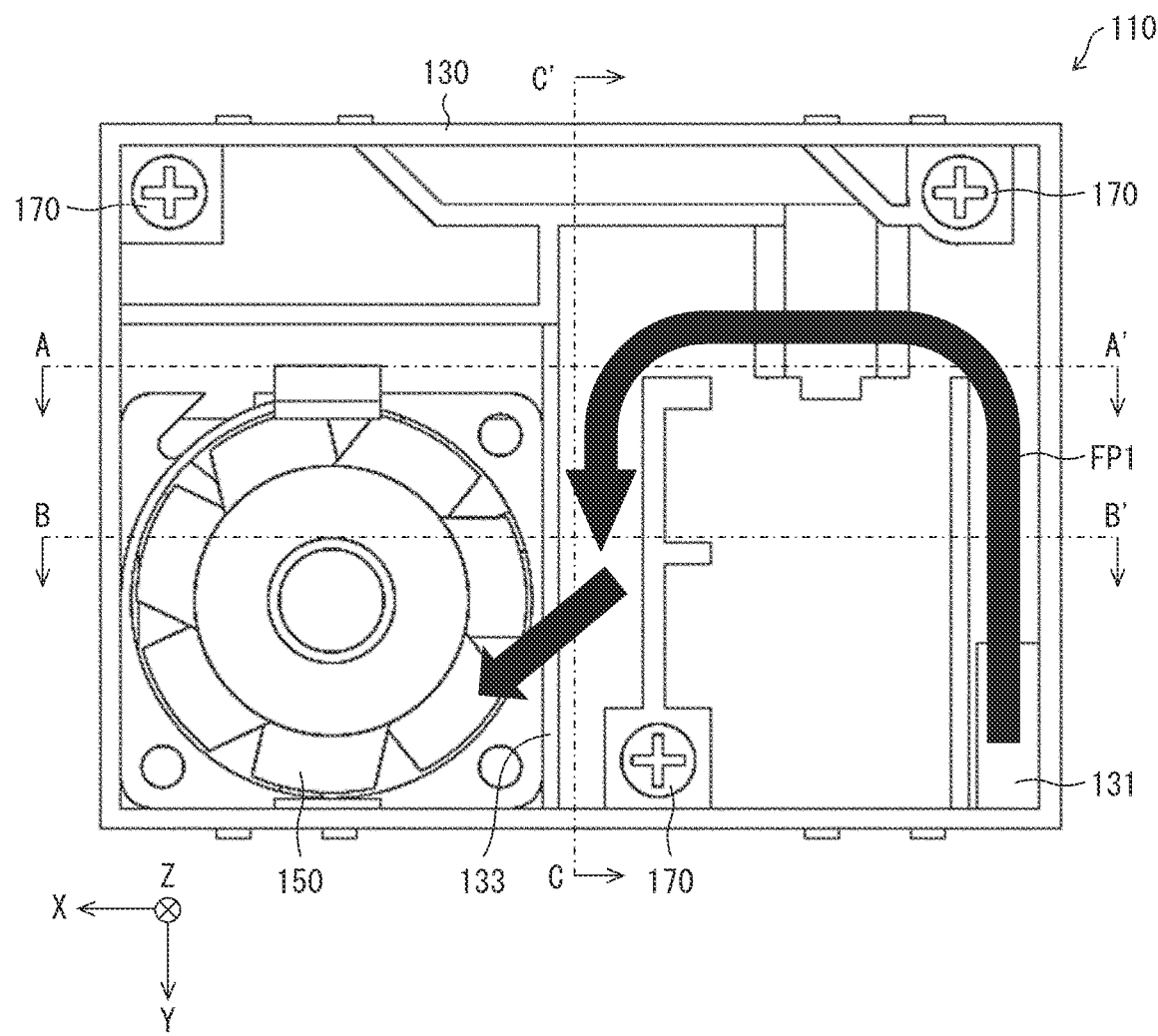
FIG. 2 is an illustration of an inner cover in accordance with Embodiment 1 of the present invention.

FIG. 2 is an illustration of the inner cover 130 in accordance with the present embodiment and shows the vertical direction flipped upside down in comparison with FIG. 1. Referring to FIG. 2, a first flow path FP1 provides a passage from the inlet 131 through the first sensor S1 so that the gas current generation mechanism 150 can discharge air to the outside. The first sensor S1 is disposed near the inlet 131.

FIG. 3 is an illustration of the rear face of the platelike member 140 in accordance with the present embodiment. Referring to FIG. 3, the first air ventilation port 141, shown as being substantially rectangular, is disposed in the upper center so as to have the lengthwise axis thereof in the Y-direction. The second air ventilation port 142, shown as being substantially rectangular, is disposed in the left center so as to have the lengthwise axis thereof in the X-direction. The first air ventilation port 141 and the second air ventilation port 142 are disposed between the first sensor S1 and the outlet 132 and, to describe it in more detail, downstream from the first sensor S1 and upstream from the gas current generation mechanism 150 in the first flow path FP1 (see FIG. 2). The second air ventilation port 142 is disposed below the gas current generation mechanism 150.

Note that the first air ventilation port 141 and the second air ventilation port 142, although both shown as being substantially rectangular in FIG. 3, may be substantially elliptical. The shape may be specified in a suitable manner.

The first air ventilation port 141 is disposed near the first sensor S1. The second air ventilation port 142 is disposed near the gas current generation mechanism 150. This arrangement enables the air having moved from the first air ventilation port 141 to below the platelike member 140 to flow through the second air ventilation port 142 into the gas current generation mechanism 150 above the platelike member 140 and discharge from the detection device 110 through the outlet 122, under the air intake force of the gas current generation mechanism 150. A second flow path FP2 provides a passage below the platelike member 140 from the first air ventilation port 141 to the second air ventilation port 142.

The detection device 110 further includes the second sensor S2 and the third sensor S3.

The second sensor S2 is disposed on the rear face of the platelike member 140, which is opposite a face of the platelike member 140 on which the first sensor S1 is provided. The second sensor S2 is disposed downstream from the first air ventilation port 141 in the second flow path FP2 (between the first air ventilation port 141 and the second air ventilation port 142).

The third sensor S3 is disposed adjacent to the second air ventilation port 142 on the rear face of the platelike member 140, which is opposite a face of the platelike member 140 on which the first sensor S1 is provided. The second air ventilation port 142 is disposed near the third sensor S3. In FIG. 3, the third sensor S3 is disposed upstream from the second air ventilation port 142 in the second flow path FP2.

In this arrangement, the second sensor S2 and the third sensor S3 are disposed on the same face of the platelike member 140 and between the first air ventilation port 141 and the second air ventilation port 142.

The first sensor S1 is the first sensor to come into contact with air in the housing and is located most upstream of the three sensors to detect, for example, dust and particles such as PM 2.5. The second sensor S2 and the third sensor S3 may be any of gas sensors (e.g., $O_2$, $O_3$, CO, $CO_2$, NOx), VOC sensors (volatile organic compound sensors), temperature sensors, humidity sensors, temperature/humidity sensors, atmospheric pressure sensors, and wind velocity sensors. In addition, both the second sensor S2 and the third sensor S3 may be provided, and alternatively, either one of the second sensor S2 and the third sensor S3 may be provided. In any case, the first sensor S1, the second sensor S2, and the third sensor S3 need only to be of different types. The combination may be specified in a suitable manner.

Note that in the present embodiment, the second sensor S2 and the third sensor S3 are disposed on the same face. Alternatively, the first sensor S1 and the third sensor S3 may be disposed on the same face, and only the second sensor S2 on another face. The locations may be specified in a suitable manner.

Figure 4:
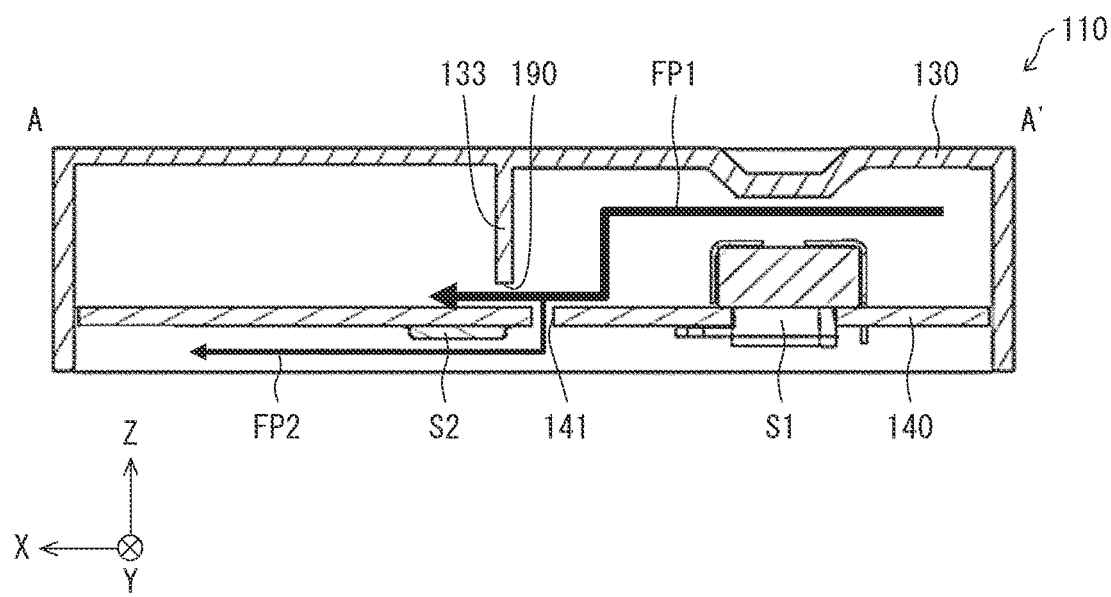
FIG. 4 is a cross-sectional view of FIG. 2, taken along line A-A'.
Figure 5:
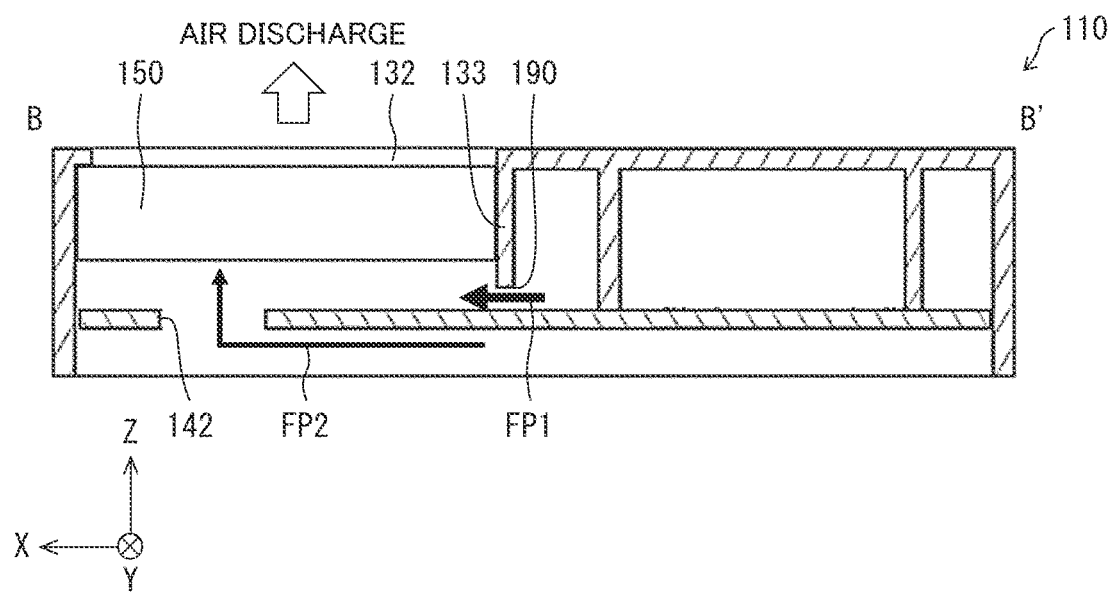
FIG. 5 is a cross-sectional view of FIG. 2, taken along line B-B'.
Figure 6:
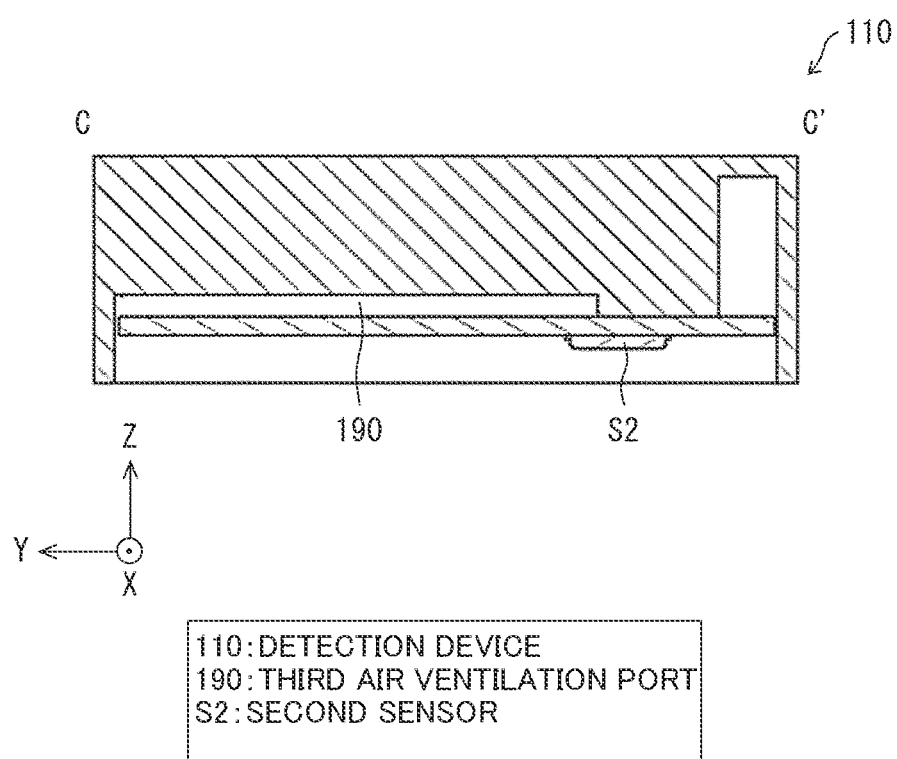
FIG. 6 is a cross-sectional view of FIG. 2, taken along line C-C'.

FIG. 4 is a cross-sectional view of FIG. 2, taken along line A-A'. FIG. 5 is a cross-sectional view of FIG. 2, taken along line B-B'. FIG. 6 is a cross-sectional view of FIG. 2, taken along line C-C'.

Referring to FIGS. 4 to 6, the air having entered the inner cover 130 through the inlet 131 (see FIG. 1) passes through the first flow path FP1 extending above the front face of the platelike member 140 and the second flow path FP2 extending below the rear face of the platelike member 140 and is discharged through the outlet 132 by the gas current generation mechanism 150.

The inner cover 130 includes, between the outlet 132 and the first sensor S1, a partition plate 133 having a third air ventilation port (ventilation port) 190.

The first flow path FP1 provides a passage for the air having passed in front of the first sensor S1 to pass through a space between the inner cover 130 and the surface of the platelike member 140 and flow into the gas current generation mechanism 150 through the third air ventilation port (ventilation port) 190 provided in the partition plate 133, so that the air can be discharged from the detection device 110 through the outlet 132 by the gas current generation mechanism 150.

The second flow path FP2 provides a passage before part of the air passing in the first flow path FP1 flows into the rear face side of the platelike member 140 through the first air ventilation port 141, passes through this rear face side, and merges into the air passing from the second air ventilation port 142 through the first flow path FP1.

The third air ventilation port (ventilation port) 190 may be larger than the first air ventilation port 141 and the second air ventilation port 142. In other words, the first air ventilation port 141 and the second air ventilation port 142 may be smaller than the third air ventilation port (ventilation port) 190. This structure enables adjusting the air flow rate. In other words, if the first air ventilation port 141 and the second air ventilation port 142 are smaller in size than the third air ventilation port (ventilation port) 190, the flow rate is slower in the second flow path FP2 than in the first flow path FP1 because of a larger fluid resistance.

Effects of Embodiment 1

(1) According to the foregoing description, measurement using the second sensor S2 and the third sensor S3 is enabled without needing to sacrifice the measurement capability of the first sensor S1, and responsiveness can be improved. In the detection device 110, the air flow path is separated into the first flow path FP1 and the second flow path FP2, and the flow rate is restrained in the second flow path FP2. Hence, dust is restrained from depositing on the surfaces of the second sensor S2 and the third sensor S3, and the second sensor S2 and the third sensor S3 are restrained from malfunctioning due to the dust deposited on the surfaces of the second sensor S2 and the third sensor S3.

To describe it in detail, the flow rate in the second flow path FP2 is lowered by reducing the opening sizes of the first air ventilation port 141 and the second air ventilation port 142 to below the size of the third air ventilation port (ventilation port) 190 in the first flow path FP1, which enables restraining dust from disadvantageously entering the second flow path FP2. Note that since the second air ventilation port 142 is an air discharge port, the second air ventilation port 142 may have as large an opening size as possible so long as the air does not flow backwards in such a manner as to allow disadvantageous entrance of dust.

(2) When the platelike member 140 is a substrate, the second sensor S2 and the third sensor S3 can be readily mounted by using the rear face of the platelike member 140 as the surface of the substrate on which circuit elements are mounted. Since components are mounted on only one surface of the substrate (platelike member 140), the cost of the substrate and fabrication is reduced, which in turn leads to reduced product cost. These are the effects achieved when the substrate forms the second flow path FP2 on the rear face of the platelike member 140.

(3) The provision of the first air ventilation port 141 between a heat generating element (especially, the light-emitting element in the first sensor S1) and the second and third sensors S2, S3 enables blocking the heat transferred from the heat generating element via the substrate (thermal conduction). Therefore, the second sensor S2 and the third sensor S3 can be restrained from malfunctioning due to the adverse effect of the heat generating element (heat).

(4) Since the second sensor S2 and the third sensor S3 are disposed in a branch flow generated in the flow path for the first sensor S1, for example, the inlet 131, the outlet 132, and the gas current generation mechanism 150 may be made common, which in turn enables product downsizing and cost reduction.

Embodiment 2

The following will describe Embodiment 2 of the present invention. For convenience of description, members that have the same function as members described in Embodiment 1 will be indicated by the same reference numerals, and description thereof is not repeated.

Figure 7:
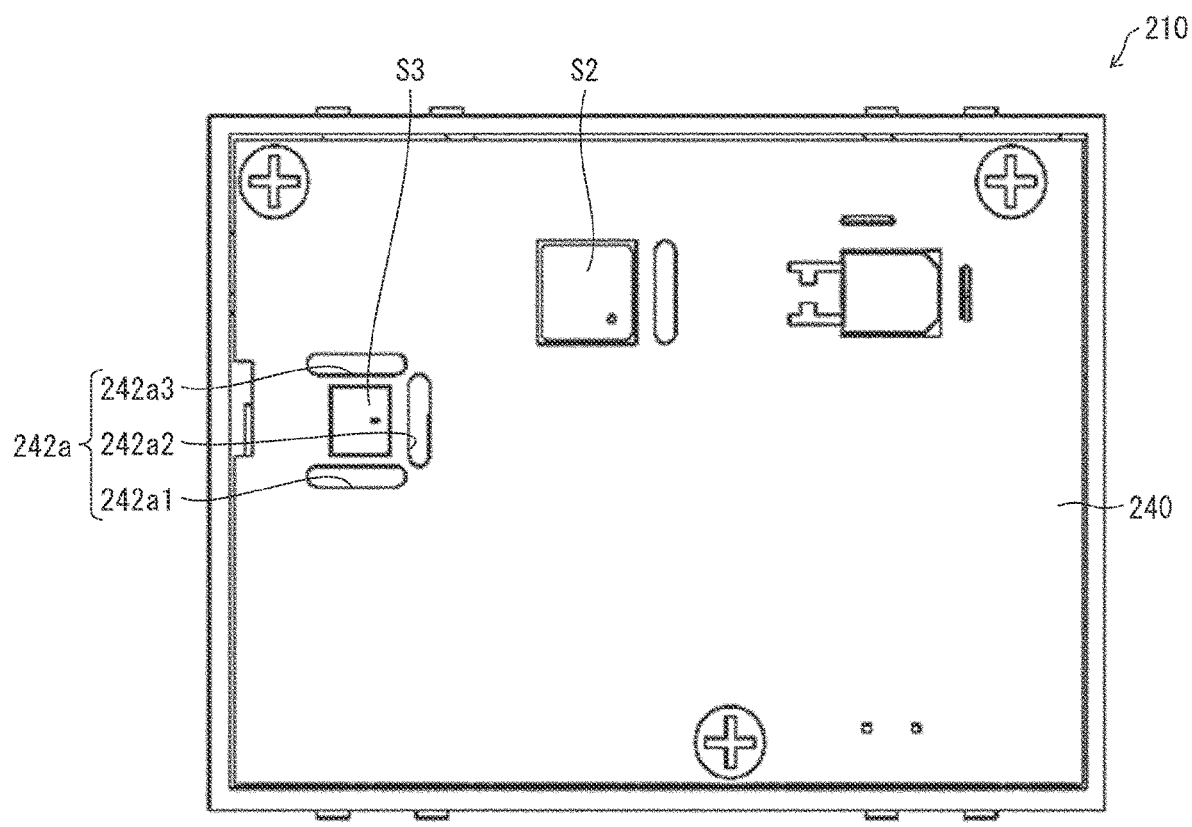
FIG. 7 is an illustration of a platelike member in accordance with Embodiment 2 of the present invention.

FIG. 7 is an illustration of a platelike member 240 in a detection device 210 in accordance with the present embodiment. FIG. 7 shows the rear face of the platelike member 240. There is provided a plurality of second air ventilation ports 242$a$ around the third sensor S3 on the rear face of the platelike member 240. Referring to FIG. 7, the second air ventilation ports 242$a$ include, for example, three air ventilation ports 242$a1$, 242$a2$, 242$a3$. The air ventilation port 242$a1$ is disposed on the Y-direction side of the third sensor S3. The air ventilation port 242$a2$ is disposed on the side opposite the X-direction of the third sensor S3. The air ventilation port 242$a3$ is disposed on the side opposite the Y-direction of the third sensor S3. In other words, the three air ventilation ports 242$a1$, 242$a2$, 242$a3$ are disposed so as to form a letter U around the third sensor S3.

Note that when there are provided three air ventilation ports in the platelike member 240, these air ventilation ports may, for example, be arranged to form, in addition to the well-ordered letter U shape shown in FIG. 7, a generally letter U shape (in other words, at least one air ventilation port of the three air ventilation ports 242$a1$, 242$a2$, 242$a3$ in FIG. 7 is displaced) or arranged so that at least one air ventilation port points in a different direction. The arrangement may be specified in a suitable manner.

Figure 8:
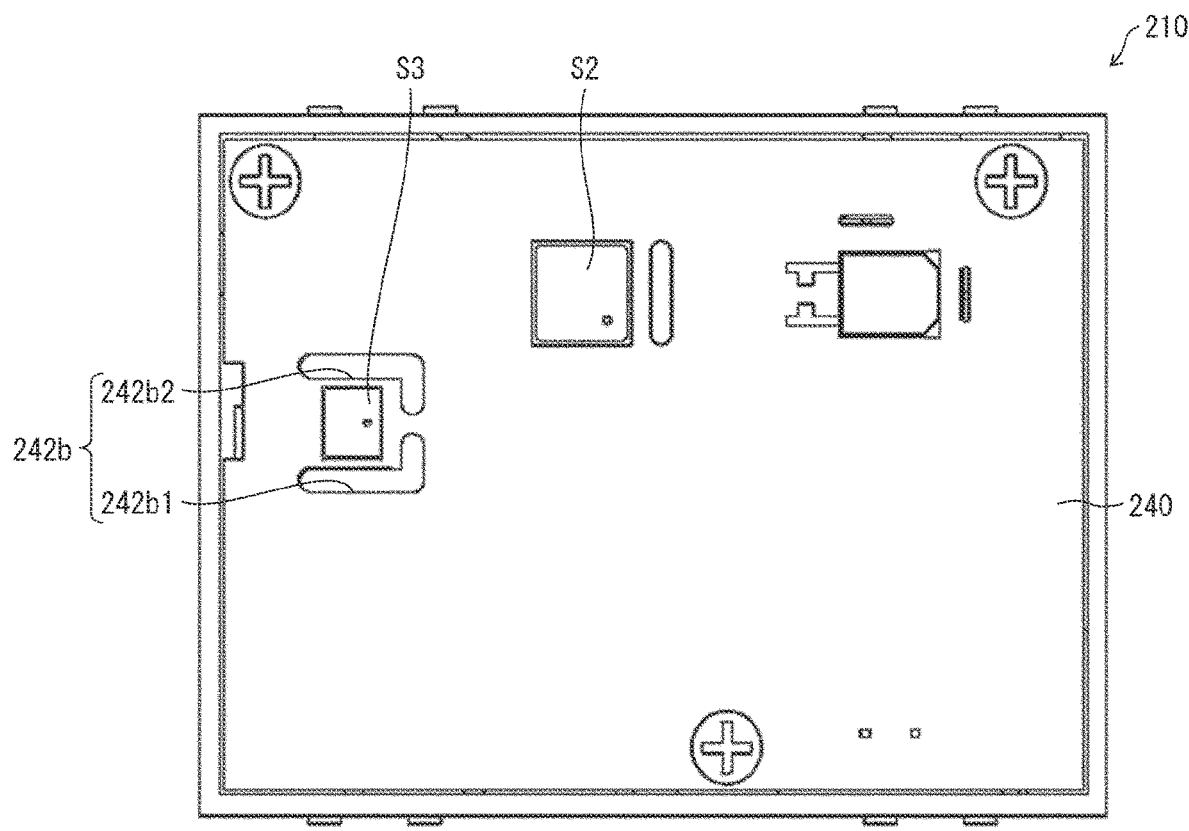
FIG. 8 is an illustration of a platelike member in accordance with Embodiment 2 of the present invention.

FIG. 8 is an illustration of another example of the platelike member 240 in the detection device 210 in accordance with the present embodiment. FIG. 8 shows the rear face of the platelike member 240. Referring to FIG. 8, a second air ventilation port 242$b$ includes, for example, two air ventilation ports 242$b1$, 242$b2$ on the rear face of the platelike member 240. The air ventilation port 242$b1$ is disposed in the left center so as to form a letter L shape in the X-direction. The air ventilation port 242$b2$ is disposed in the left center so as to form a reversed letter L shape in the X-direction. In other words, the two air ventilation ports 242b1, 242b2 are arranged so as to form a letter U shape around the third sensor S3.

Note that when there are provided two air ventilation ports in the platelike member 240, these air ventilation ports may, for example, be arranged to form, in addition to the letter L and reversed letter L shapes shown in FIG. 8, a generally letter L shape (in other words, one air ventilation port of the three air ventilation ports 242a1, 242a2, 242a3 is eliminated in FIG. 7) or arranged so as to be parallel to each other. The arrangement may be specified in a suitable manner.

Effects of Embodiment 2

(1) According to the foregoing description, the provision of the second air ventilation ports 242a, 242b enables blocking or restraining thermal conduction from the heat generating element via the platelike member 240. Therefore, the second sensor S2 can be restrained from malfunctioning and property variations (drifting) due to the adverse effect of heat generation.
(2) The second sensor S2 and the third sensor S3 are not the same sensors and assumed to be sensors for totally different purposes. For instance, the second sensor S2 is a gas sensor, and the third sensor S3 is a temperature/humidity sensor. A temperature/humidity sensor is sensitive to ambient temperature changes. Accordingly, as shown in FIG. 7, the platelike member 240 has three slits as the second air ventilation ports 242a, to be more resistant to adverse thermal effects from other elements and sensors. In addition, as shown in FIG. 8, the platelike member 240 has two slits as the second air ventilation port 242b, to be more resistant to adverse thermal effects from other elements and sensors.
(3) Here, the slits and the air ventilation ports are common, which is a feature. In other words, the use of the slits as air ventilation ports eliminates the need to provide additional slits for heat dissipation purposes.

Embodiment 3

The following will describe Embodiment 3 of the present invention. For convenience of description, members that have the same function as members described in Embodiments 1, 2 will be indicated by the same reference numerals, and description thereof is not repeated.

Figure 9:
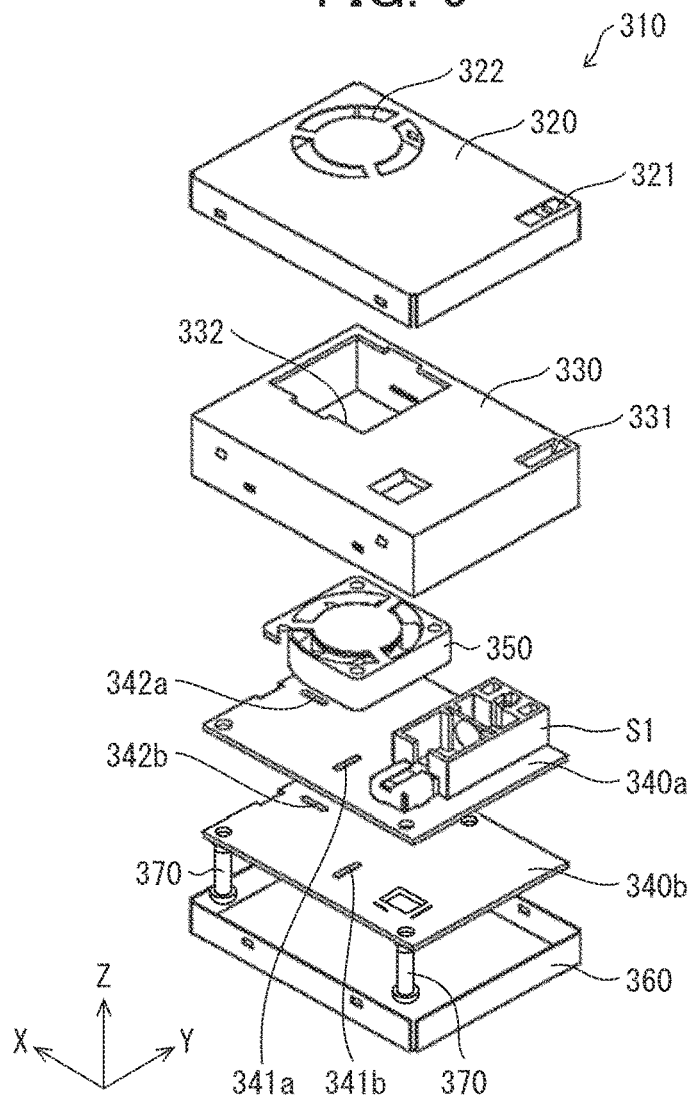
FIG. 9 is an exploded perspective view of a detection device in accordance with Embodiment 3 of the present invention.

FIG. 9 is an exploded perspective view of a detection device 310 in accordance with the present embodiment. Referring to FIG. 9, the detection device 310 includes a stack of a first platelike member 340a and a second platelike member 340b in the housing. The first platelike member 340a provides a base plate to which, for example, a gas current generation mechanism 350 and the first sensor S1 are mounted. The first platelike member 340a has a first air ventilation port 341a and a second air ventilation port 342a. The second platelike member 340b is disposed on the rear face side of the first platelike member 340a. The second platelike member 340b has a first air ventilation port 341b and a second air ventilation port 342b. The second platelike member 340b is supported via screws 370 provided inside a rear cover 360.

Figure 10:
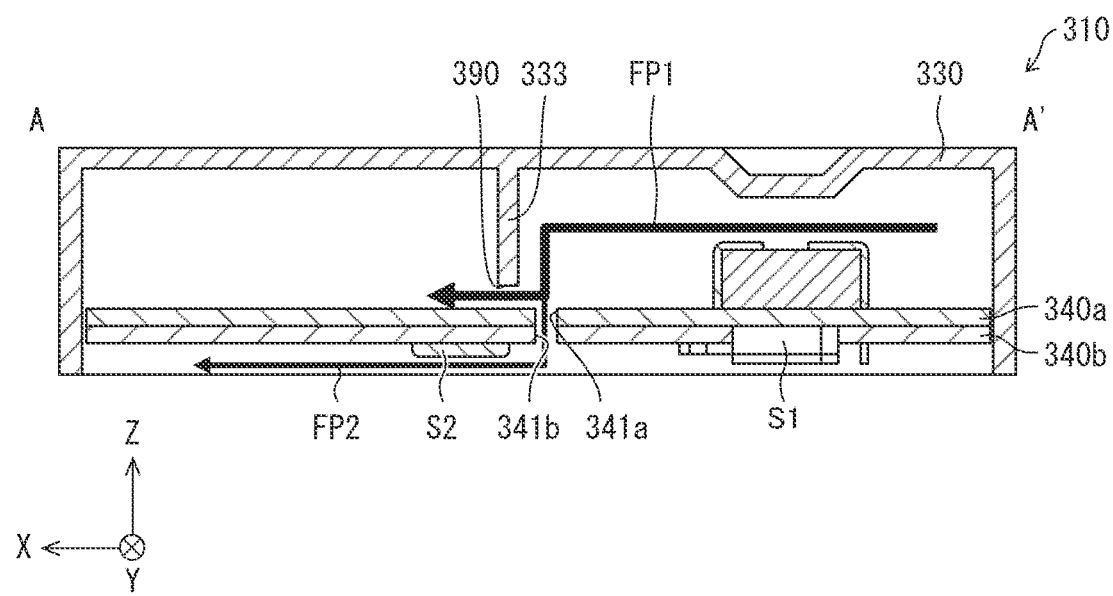
FIG. 10 is a cross-sectional view corresponding to FIG. 4, taken along line A-A', in accordance with Embodiment 3 of the present invention.
Figure 11:
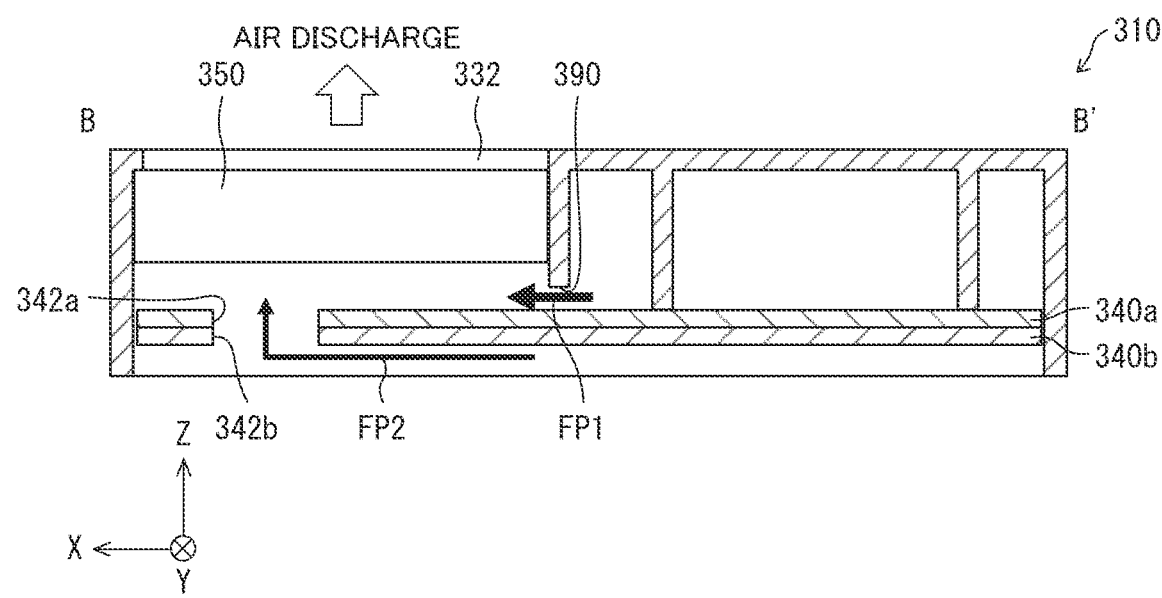
FIG. 11 is a cross-sectional view corresponding to FIG. 5, taken along line B-B', in accordance with Embodiment 3 of the present invention.
Figure 12:
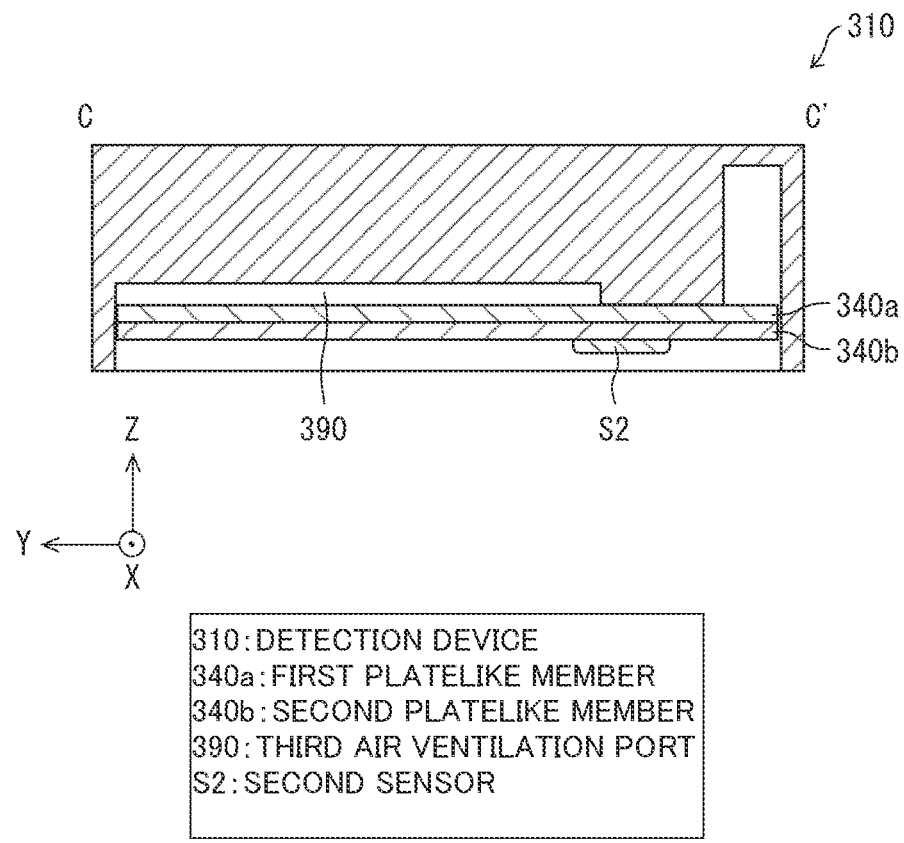
FIG. 12 is a cross-sectional view corresponding to FIG. 6, taken along line C-C', in accordance with Embodiment 3 of the present invention.

FIG. 10 is a cross-sectional view corresponding to FIG. 4, taken along line A-A', in accordance with the present embodiment. FIG. 11 is a cross-sectional view corresponding to FIG. 5, taken along line B-B', in accordance with the present embodiment. FIG. 12 is a cross-sectional view corresponding to FIG. 6, taken along line C-C', in accordance with the present embodiment.

Referring to FIGS. 10 to 12, the first platelike member 340a and the second platelike member 340b are disposed in contact with each other. The air having entered an inner cover 330 through inlets 321, 331 separates into the first flow path FP1 extending above the first platelike member 340a and the second flow path FP2 extending through the first air ventilation ports 341a and 341b and along the rear face side of the second platelike member 340b. The air having passed through the first flow path FP1 and the second flow path FP2 is discharged from the detection device 310 through an outlet 332 by the gas current generation mechanism 350. As in the first embodiment, the inner cover 330 includes, between the outlet 332 and the first sensor S1, a partition plate 333 having a third air ventilation port (ventilation port) 390, and the first flow path FP1 is a passage for the air through the third air ventilation port.

The second sensor S2 is disposed on a face of the second platelike member 340b opposite the face thereof facing the first platelike member 340a and between the first air ventilation port 341b and the second air ventilation port 342b.

Effects of Embodiment 3

When the second platelike member 340b is a substrate, since the first platelike member 340a and the second platelike member 340b are disposed in contact with each other, the first platelike member 340a covers the second platelike member 340b which is a substrate. Therefore, dust can be prevented from depositing on the surface of the second platelike member 340b. In addition, since the first platelike member 340a covers the second platelike member 340b, it becomes easier to perform maintenance jobs on the second platelike member 340b which is a substrate.

Note that there may be provided a stack of platelike members. Two platelike members are not necessarily provided as described above; a stack of three or more platelike members may be provided. In such a case, dust can be prevented from depositing on the platelike members in all the layers except for the topmost layer, in other words, on the platelike members in the second and subsequent layers from the top, thereby facilitating maintenance jobs.

Embodiment 4

The following will describe Embodiment 4 of the present invention. For convenience of description, members that have the same function as members described in Embodiments 1 to 3 will be indicated by the same reference numerals, and description thereof is not repeated. The present embodiment will describe variation examples of the air ventilation port.

Figure 13:
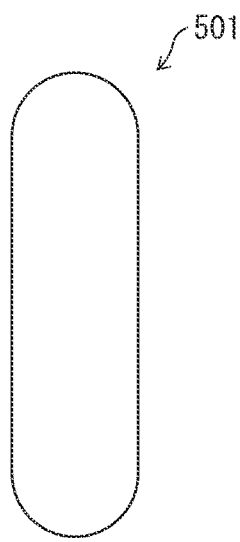
FIG. 13 is an illustration of a working example of an air ventilation port in accordance with Embodiment 4 of the present invention.

FIG. 13 is an illustration of Example 1 of the air ventilation port in accordance with the present embodiment. Referring to FIG. 13, an air ventilation port 501 in accordance with Example 1 includes a single opening. The air ventilation port 501 is a typical example of the air ventilation port.

Figure 14:
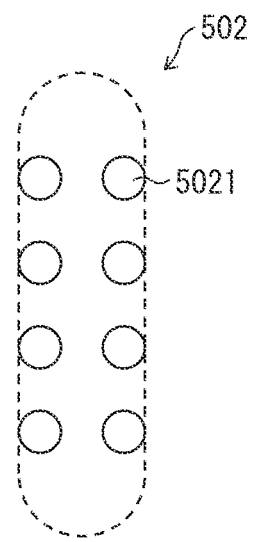
FIG. 14 is an illustration of a working example of an air ventilation port in accordance with Embodiment 4 of the present invention.

FIG. 14 is an illustration of Example 2 of the air ventilation port in accordance with the present embodiment. Referring to FIG. 14, an air ventilation port 502 in accordance with Example 2 includes a plurality of fine pores 5021. The air ventilation port 502 is a typical example of the air ventilation port. At least one of the first air ventilation ports 141, 341a, 341b, the third air ventilation ports 190, and a third air ventilation port 390 may have the same structure as the air ventilation port 502.

Figure 15:
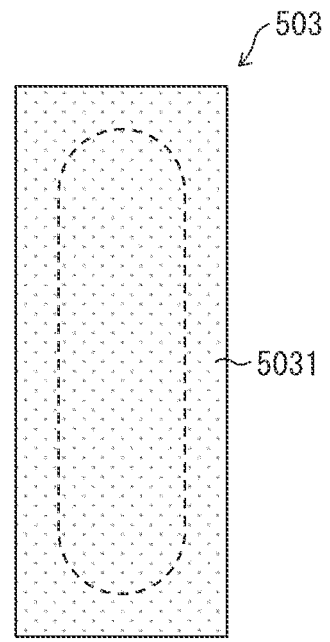
FIG. 15 is an illustration of a working example of an air ventilation port in accordance with Embodiment 4 of the present invention.

FIG. 15 is an illustration of Example 3 of the air ventilation port in accordance with the present embodiment. Referring to FIG. 15, an air ventilation port 503 in accordance with Example 3 includes a filter 5031. The air ventilation port 503 is a typical example of the air ventilation port. At least one of the first air ventilation ports 141, 341a, 341b and the third air ventilation ports 190, 390 may have the same structure as the air ventilation port 503.

Note that Examples 1, 2, and 3 may be used either in combination or individually.

According to Examples 2 and 3, dust can be restrained from passing.

Embodiment 5

The following will describe Embodiment 5 of the present invention. For convenience of description, members that have the same function as members described in Embodiments 1 to 4 will be indicated by the same reference numerals, and description thereof is not repeated. The present embodiment will describe variation examples of a partition plate 433 on an inner cover 430.

Figure 16:
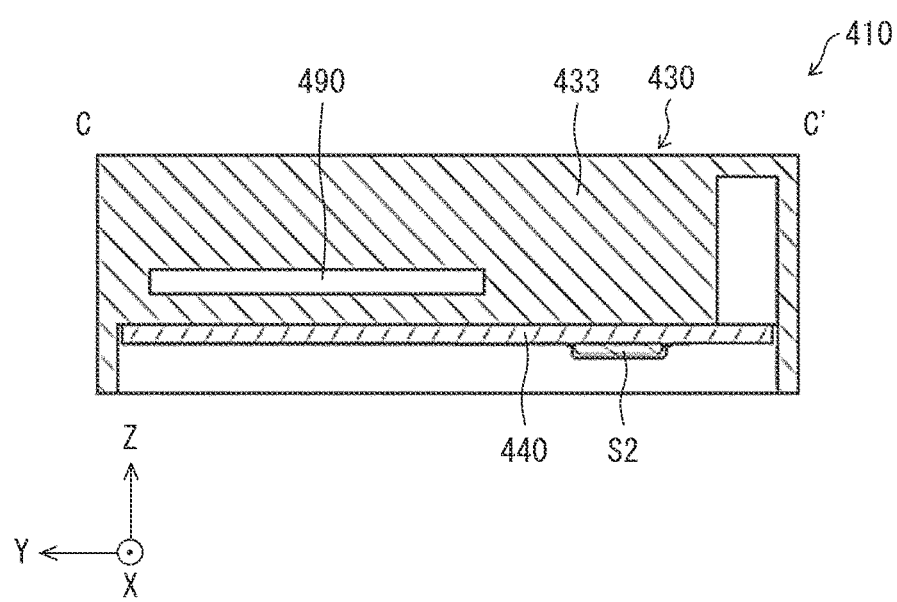
FIG. 16 is an illustration of a partition plate on an inner cover in accordance with Embodiment 5 of the present invention.

FIG. 16 is an illustration of the partition plate 433 on the inner cover 430 in a detection device 410 in accordance with the present embodiment. Referring to FIG. 16, the partition plate 433 on the inner cover 430 has a third air ventilation port (ventilation port) 490 displaced toward the center of the partition plate 433 when compared with Embodiments 1 to 3. A gas current generation mechanism (not shown), although being disposed on a platelike member 440 side, produces similar effects. The third air ventilation port (ventilation port) 490 may be disposed on the platelike member 440 side of the partition plate 433 or near the center of the partition plate 433.

General Description

The present invention, in aspect 1 thereof, is directed to a detection device including: a housing including an air intake port and an air discharge port; a platelike member having a first air ventilation port and a second air ventilation port, the platelike member being provided inside the housing; a first sensor provided on an air intake port side of the first air ventilation port on a front face of the platelike member; and a second sensor provided between the first air ventilation port and the second air ventilation port on a rear face of the platelike member.

This structure enables gas measurement using the second sensor without needing to sacrifice the gas measurement capability of the first sensor and enables improving responsiveness. The structure also enables a single port to serve as both an air intake port and an air discharge port for supplying air to the two sensors, thereby enabling product downsizing and cost reduction.

In aspect 2 of the present invention, the detection device of aspect 1 may be configured such that the housing further includes, between the air discharge port and the first sensor, a partition plate including a third air ventilation port, and the third air ventilation port is larger than the first air ventilation port and the second air ventilation port.

This structure enables adjusting the flow rate of a gas. In other words, the provision of a larger third air ventilation port than the first air ventilation port and the second air ventilation port leads to a fluid resistance that is larger in the first air ventilation port and the second air ventilation port that are smaller than the third air ventilation port, thereby restraining dust from disadvantageously entering the second sensor.

In aspect 3 of the present invention, the detection device of aspect 1 or 2 may be configured such that the housing further includes a gas current generation mechanism configured to vent air out of the housing through the air discharge port, and the second air ventilation port is provided below the gas current generation mechanism.

This structure enables efficient air discharge by the gas current generation mechanism.

In aspect 4 of the present invention, the detection device of any of aspects 1 to 3 may be configured such that the platelike member includes a stack of platelike members.

This structure includes a stack of platelike members. Therefore, dust can be prevented from depositing on the platelike member in all the layers except for the topmost layer (in the second and subsequent layers from the top), thereby facilitating maintenance jobs.

In aspect 5 of the present invention, the detection device of aspect 4 may be configured so as to further include a third sensor provided on a same face as the second sensor, wherein the second air ventilation port is provided near the third sensor.

This structure includes the second air ventilation port near the third sensor, thereby enabling the third sensor to reliably perform gas measurement.

In aspect 6 of the present invention, the detection device of aspect 5 may be configured such that the second air ventilation port includes a plurality of second air ventilation ports provided around the third sensor.

This structure includes a plurality of second air ventilation ports around the third sensor, thereby enabling the third sensor to reliably perform gas measurement.

In aspect 7 of the present invention, the detection device of aspect 2 may be configured such that at least any one of the first air ventilation port and the third air ventilation port includes a plurality of fine pores.

This structure enables restraining dust from passing.

In aspect 8 of the present invention, the detection device of aspect 2 may be configured such that at least any one of the first air ventilation port and the third air ventilation port includes a filter.

This structure enables further restraining dust from passing.

The present invention, in aspect 9 thereof, is directed to an electronic apparatus including the detection device of any of aspects 1 to 8.

The present invention is not limited to the description of the embodiments above and may be altered within the scope of the claims. Embodiments based on a proper combination of technical means disclosed in different embodiments are encompassed in the technical scope of the present invention. Furthermore, new technological features can be created by combining different technical means disclosed in the embodiments.

While there have been described what are at present considered to be certain embodiments of the invention, it will be understood that various modifications may be made thereto, and it is intended that the appended claims cover all such modifications as fall within the true spirit and scope of the invention.

What is claimed is:
1. A detection device comprising:
a housing including an air intake port and an air discharge port;

a substrate having a first air ventilation port and a second air ventilation port, the substrate being provided inside the housing;

a first sensor provided on an air intake port side of the first air ventilation port on a front face of the substrate; and a second sensor provided between the first air ventilation port and the second air ventilation port on a rear face of the substrate, wherein a first flow path is formed, such that a first air flows in a direction along the front face of the substrate, and a second flow path is formed, such that a second air flows in a direction along the rear face of the substrate, and the second flow path is branched from the first flow path via the first air ventilation port, and merged into the first flow path via the second air ventilation port.

2. The detection device according to claim 1, wherein
the housing further includes, between the air discharge port and the first sensor, a partition plate including a third air ventilation port, and
the third air ventilation port is larger than the first air ventilation port and the second air ventilation port.

3. The detection device according to claim 2, wherein at least any one of the first air ventilation port and the third air ventilation port includes a plurality of fine pores.

4. The detection device according to claim 2, wherein at least any one of the first air ventilation port and the third air ventilation port includes a filter.

5. The detection device according to claim 1, wherein
the housing further includes a gas current generation mechanism configured to vent air out of the housing through the air discharge port, and
the second air ventilation port is provided below the gas current generation mechanism.

6. The detection device according to claim 1, wherein the substrate includes a stack of platelike members.

7. The detection device according to claim 1, further comprising a third sensor provided on a same face as the second sensor, wherein the second air ventilation port is provided near the third sensor.

8. The detection device according to claim 7, wherein the second air ventilation port includes a plurality of second air ventilation ports provided around the third sensor.

9. An electronic apparatus comprising the detection device according to claim 1.

* * * * *